(12) United States Patent
Cuppen et al.

(10) Patent No.: US 10,128,641 B2
(45) Date of Patent: Nov. 13, 2018

(54) PIVOT CABLE SOLUTION

(71) Applicant: KONINKLIJKE PHILIPS N.V., Eindhoven (NL)

(72) Inventors: Martinus Antonius Maria Cuppen, Eindhoven (NL); Walter Peter Bleyen, Eindhoven (NL); Wilhelmus Gerardus Theodorus Lommen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 5 days.

(21) Appl. No.: 15/105,073

(22) PCT Filed: Dec. 10, 2014

(86) PCT No.: PCT/EP2014/077207
§ 371 (c)(1),
(2) Date: Jun. 16, 2016

(87) PCT Pub. No.: WO2015/091152
PCT Pub. Date: Jun. 25, 2015

(65) Prior Publication Data
US 2016/0322793 A1    Nov. 3, 2016

(30) Foreign Application Priority Data
Dec. 19, 2013    (EP) ..................................... 13198597

(51) Int. Cl.
*H01B 17/58*        (2006.01)
*H02G 3/04*         (2006.01)
*H02G 3/32*         (2006.01)
*A61B 6/00*         (2006.01)
*H01B 17/56*        (2006.01)
*H02G 11/00*        (2006.01)

(52) U.S. Cl.
CPC ............. *H02G 3/04* (2013.01); *A61B 6/4441* (2013.01); *H01B 17/56* (2013.01); *H02G 3/32* (2013.01); *H02G 11/00* (2013.01)

(58) Field of Classification Search
CPC . H02G 3/04; H02G 3/32; H02G 11/00; A61B 6/4441; H01B 17/56
See application file for complete search history.

(56) References Cited

U.S. PATENT DOCUMENTS

| | | | |
|---|---|---|---|
| 1,089,642 A | | 3/1914 | Honold |
| 4,114,043 A | | 9/1978 | Gansfried |
| 4,705,243 A | | 11/1987 | Hartmann |
| 4,802,197 A | | 1/1989 | Juergens |
| 6,071,148 A | * | 6/2000 | Radliff ............... H01R 13/5221 439/587 |
| 6,609,826 B1 | | 8/2003 | Fujii |
| 7,518,058 B1 | | 4/2009 | Hagbrandt |

(Continued)

FOREIGN PATENT DOCUMENTS

| | | |
|---|---|---|
| CA | 2475261 A1 | 1/2006 |
| DE | 1770658 U | 7/1958 |

(Continued)

*Primary Examiner* — Steven T Sawyer

(57) ABSTRACT

A cable spacer (200) for managing cable work in particular in machinery having a rotatable part. The spacer is capable of receiving at least part of a cable bundle to ensure that a clearance or distance between the cables is maintained even during torsion or other motion of the cable bundle.

17 Claims, 9 Drawing Sheets

(56) References Cited

U.S. PATENT DOCUMENTS

| | | |
|---|---|---|
| 7,543,986 B2 | 6/2009 | Saffer |
| 8,344,255 B2 | 1/2013 | Wickhorst |
| 2005/0263316 A1 | 12/2005 | Matsumoto |
| 2007/0007397 A1* | 1/2007 | Nelson ................. F16L 3/2235 248/68.1 |
| 2007/0246613 A1* | 10/2007 | Kennedy ................. H02G 3/32 248/56 |
| 2010/0032531 A1 | 2/2010 | Getts |
| 2011/0042529 A1* | 2/2011 | Walter ................... F16L 3/223 248/68.1 |
| 2012/0085078 A1 | 4/2012 | Rijken |
| 2015/0001354 A1 | 1/2015 | Brabander et al. |

FOREIGN PATENT DOCUMENTS

| | | |
|---|---|---|
| DE | 102012001408 A1 | 7/2013 |
| WO | 198501686 A1 | 4/1985 |
| WO | 200079660 A1 | 12/2000 |

* cited by examiner

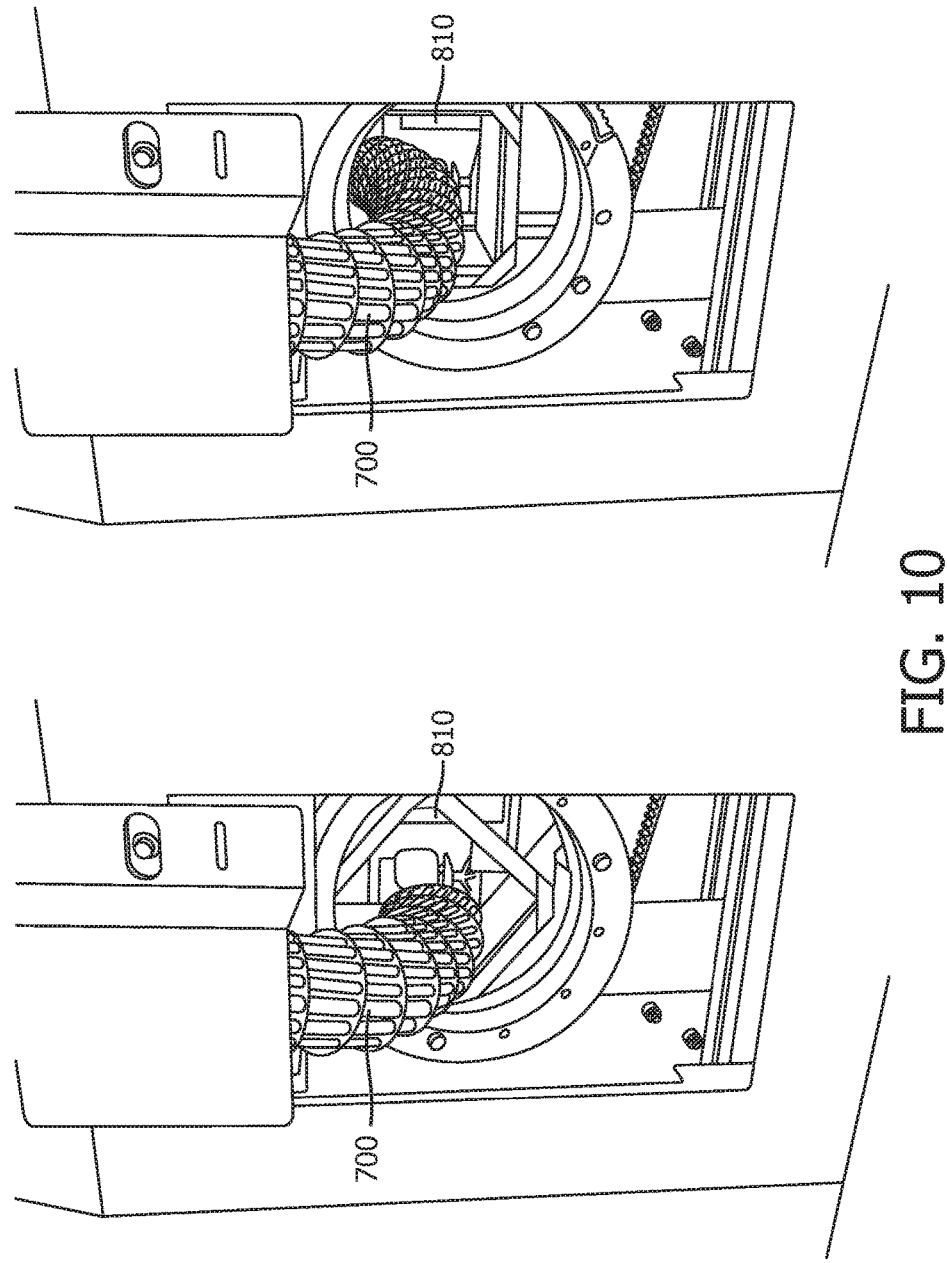

PIVOT CABLE SOLUTION

CROSS-REFERENCE TO PRIOR APPLICATIONS

This application is the U.S. National Phase application under 35 U.S.C. § 371 of International Application No. PCT/EP2014/077207, filed on Dec. 10, 2014, which claims the benefit of European Patent Application No. 13198597.0, filed on Dec. 19, 2013. These applications are hereby incorporated by reference herein.

FIELD OF THE INVENTION

The invention relates to a cable spacer, to a cable spacer arrangement or system, and to machinery having a rotatable part.

BACKGROUND OF THE INVENTION

In today's catheterization laboratories ("cath labs") there are tight space constraints for personnel and equipment. Imaging system in the cath lab usually have the largest footprint and are often found quite "bulky" with associated cable work more often than not getting into the way of already stressed personnel when dealing with critical cases and ever raising clinical workloads. Also, maintenance in particular cleaning chores, important as they are to maintain the required hygienic standards, are often bothersome and time consuming, which reduces the cath lab's through-put capability.

SUMMARY OF THE INVENTION

There may therefore be a need for a different cable management approach that addresses at least the above noted needs.

The object of the present invention is solved by the subject matter of the independent claims where further embodiments are incorporated in the dependent claims. It should be noted that the following described aspect of the invention equally applies to the cable spacer arrangement and to the machinery having a rotatable part.

According to a first aspect of the invention, there is provided a cable spacer for receiving a plurality of cables. At least a part of each cable is received therein. The cable spacer is configured to maintain a clearance or safety distance among the cables during motion of at least one of said cables or during motion of the spacer: The cable spacer has at least three recesses formed in an edge of said cable spacer for receiving at least three cables, said recesses arranged so as to enclose a central area of the cable spacer.

The clearance or safety distance between each of the cables is maintained even under torsional motion or another challenging motion of the cable (bundle). No chaffing between cable jackets can occur and friction is minimized. According to one embodiment, some or all of the recesses have a neck portion to securely hold the cables in place when received in the respective recesses.

Because the recesses are arranged or grouped (preferably but not necessary equidistantly and/or symmetrically) around the center of the spacer, the plurality of cables delimit or enclose volume. The arrangement affords a favorable behavior when the bundle is to take up torsion, bending or twisting and is to assume different curvatures during the course of the motion.

According to one embodiment, the spacer is openable and closable. More particularly, the spacer forms two wing or jaw portions when open so as to receive a cable or to allow removal of a cable. Mating closure elements are formed in the wing or jaw portions that are configured to engage when the wing portions are moved into contact to close the spacer.

Maintenance of the cable work is easy and hassles as there is no need for having to "thread" the cables onto the spacers. The opening/closing is quick because no tools are required and the cables can be removed outside the spacer when opened.

According to one embodiment, the spacer includes a pivot point and is openable and closable around said pivot point.

According to one embodiment, the pivot point is formed in said edge or is formed away from said edge.

According to one embodiment, the edge is curved or polygonal.

In particular the edge follows a generally curved course which allows tight packing of bundles of cables in the spacer.

According to one embodiment, the edge follows a meandering pattern.

According to one embodiment, the pattern is formed from crests and troughs, wherein each of the cable receiving recesses is defined by two crests with a respective one of the troughs therebetween.

According to one embodiment, the cable spacer is formed from an oval or spherical disk when closed.

According to one embodiment, the cable spacer has a plurality of through-holes or slots arranged so as to enclose the central area.

According to one embodiment, each of two jaw portions has a necked recess. The two recesses form the or a necked through-hole or slot through the spacer when the cable spacer is closed: The through-hole is configured to receive two or more cables and the cables so received are prevented from touching each other by at least one neck portion formed in the periphery of at least one the necked recesses. The cables are thereby safely retained in the spacer rather than "popping out" when the spacer is opened.

According to one embodiment, the closure elements are any one of i) a snap fit or ii) a dovetail arrangement. The closure element may be formed integrally in the or an edge of the spacer.

According to one embodiment, the cable spacer comprises additionally a peripheral retainer member removably receivable around the edge to hold in place a cable when received in one of the recesses.

According to one embodiment, the cable spacer is formed monolithically from one piece with the retainer member.

According to one embodiment, the cable spacer has a nested structure comprising an annular outer portion and a removable inner portion, the inner portion having one or more recesses to receive one or more cables.

The solution affords a modular design and further increases accessibility of the cables.

According to one embodiment, the cable spacer is formed from a plastic material or other suitable material such a composite aluminum or other.

According to one embodiment, the cable spacer is manufactured by molding, for instance injection molding but also other molding techniques are envisaged. Also manufacturing by cutting is envisaged in some embodiments.

According to one aspect there is provided a spacer arrangement for receiving a plurality of cables, comprising a plurality of spacers according to any of the embodiments described above and arranged along the length of the cables at a distance to each other when the spacer arrangement is in use.

According to one embodiment, the spacer arrangement or system includes a distance element arranged between two neighboring ones of the plurality of the spacers so as to maintain a pre-defined distance between the neighboring spacers during motion of the plurality of cables and/or spacers.

According to one embodiment, the distance element is movably received in both of the neighboring spacers.

According to one embodiment, the distance element is formed by a central cable that is run through respective central through-holes arranged in the spacers, with the spacers fixedly arranged on said central cable.

According to one aspect there is provided a spacer arrangement or system for receiving a plurality of cables, comprising a plurality of spacers each for receiving at least parts of said plurality of cables, the spacers configured to maintain a clearance among the cables during motion of at least one of said cables or during motion of at least one of the spacers, the plurality of spacers arranged along the length of the cables at a fixed distance to each other when the spacer arrangement is in use, wherein said distances are maintained during said motion.

The plurality of spacers forms a "skeletal structure" for the cable bundle. The spacers may or may not be equidistantly arranged along the cables' length. A distance between the spacers may be maintained by rigid distance pieces arranged between neighboring spacers or by fixing the spacers to a cable for instance the central one of the cables in the bundle.

According to one aspect there is provided a medical imaging equipment or other medical or non-medical machinery having at least one movable component with a plurality of cables connected to said component. The plurality of cables is being moved when said competent is moving. The plurality of cables is received in at least one cable spacer, preferably in a plurality of cables spacers or arrangement as described herein. The cables so received are run internally in a housing of the medical imaging equipment.

As will be appreciated from the following description, a new cable management solution is proposed herein which can be used for guiding cables through pivoting points between machinery with relative motion in particular for instance, between a static part and a moving part. The solution proposed herein may be put to good use in all kinds of rotating systems, medical or non-medical such as robots etc.

BRIEF DESCRIPTION OF THE DRAWINGS

Exemplary embodiments of the invention will now be described with reference to the following drawings wherein:

FIG. 10 shows different use of the rotating system as per FIG. 9.

DETAILED DESCRIPTION OF EMBODIMENTS

Figure 1:
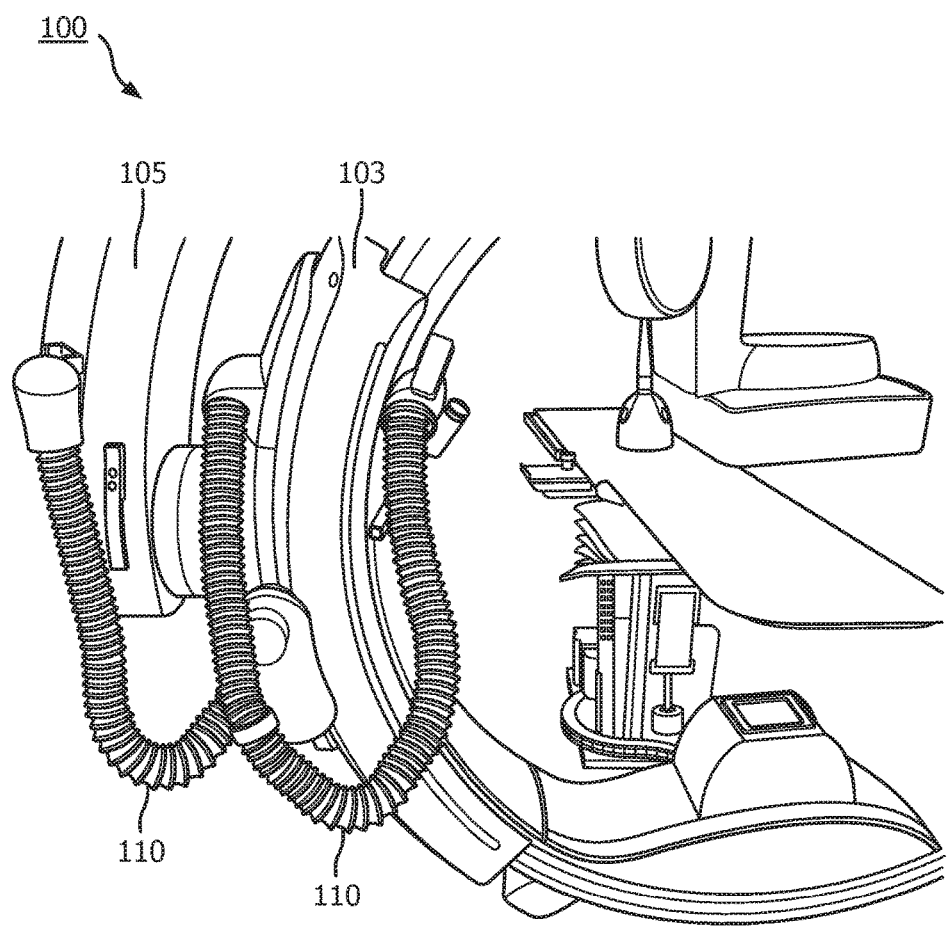
FIG. 1 shows an interventional x-ray imager of the C arm type.

With reference to FIG. 1, there is shown an existing x-ray imaging system for instance an interventional x-ray imager apparatus. Very broadly the apparatus includes a cradle or "sleeve" 105 with a housing in which a C-arm is slideably arranged. The moving C-arm 103 is connected via electrical cables with cradle 105 forming a static part of the imager. In existing system as shown in FIG. 1, the cable work is run on the outside of the imager's housing within flexible cable tubing. The cable tubing includes corrugations that afford flexibility and allow the tubing to form configurations at the required curvature as the arm moves relative to the cradle. It has been observed however, that the cable receiving tubing 110 takes up considerable space in already tight cath lab environments in which those imagers are normally used and also that dirt, deposits and liquids tend to accumulate in the corrugations. This makes maintenance, in particular cleaning, cumbersome.

Figure 2A:
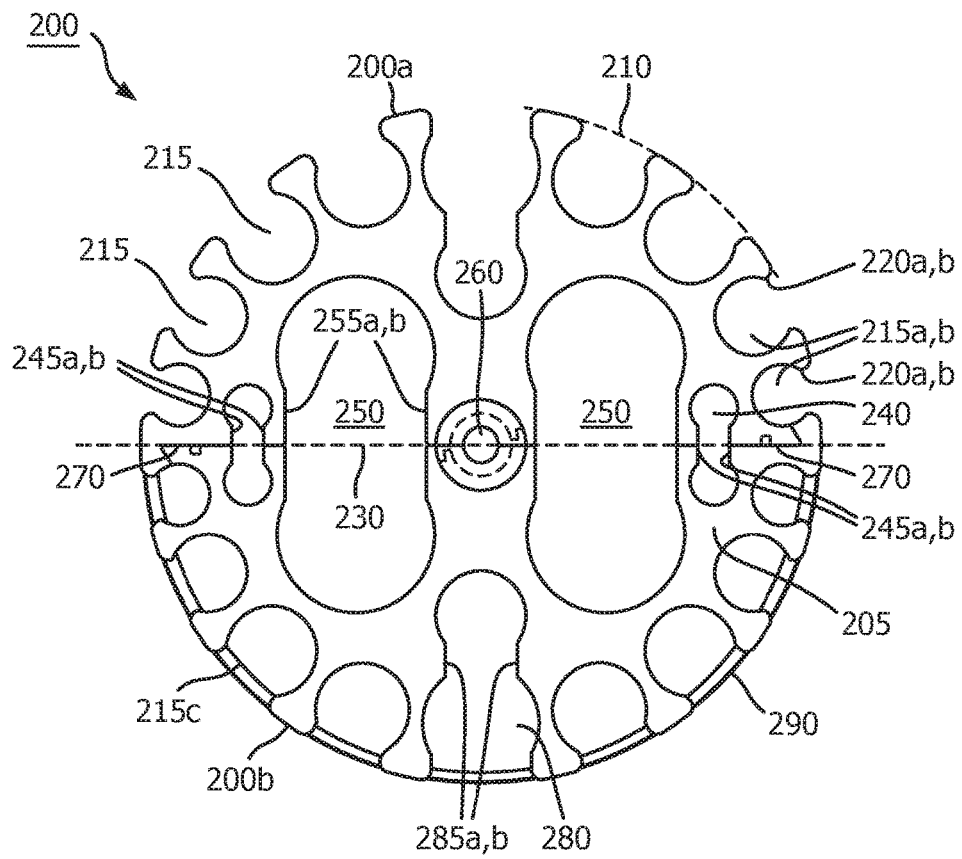
FIG. 2 shows different views of a cable spacer according to one embodiment.

With reference to FIG. 2A, there is shown a cable spacer 200 in plan view according to one embodiment. Cable spacer 200 comprises a base member 205 which in one embodiment is disc shaped as shown in FIG. 2. Base number 205 has an edge 210 outlined in dashed lines. Edge 210 follows a circular path in the disk shaped embodiment of FIG. 2A but this may not be so necessarily as other shapes than disc shaped are also envisaged therein. For instance, base member may 205 be oval, egg shaped or otherwise. In general, base member 205 has a curved edge, partly or throughout, although base members of polygonal shape are also envisaged herein.

Base number 205 may be formed by injection molding from a suitable plastic material of suitable rigidity but other materials such aluminum or composite materials, in particular carbon fiber reinforced composite materials are likewise envisaged herein. Suitable plastic materials include PC (polycarbonate), ABS (acrylonitrile butadiene styrene), and PA (polyamide) or a mixture of any of these. In one embodiment the disc has a diameter of about 10 cm and a thickness of about 5 mm. However, this is purely exemplary and in no way limiting, that is, other dimensionings are likewise envisaged herein.

Spacer 200 is configured to receive a plurality of electrical cables, in particular, a bundle of electrical cables. As can be seen from the construction in FIG. 2A, the spacer allows receiving the cables at its periphery or edge 210 but also internally, that is, away from the edge 210 in a plurality of through holes or slots formed in spacer 200's base member 215.

The cables are received at the periphery or edge in a plurality of recesses 215 formed in the edge 210 of the base member 205. In one embodiment the recesses are equidistantly spaced and are arranged all along the edge. Again, this is one exemplary embodiment only, as non-equidistant arrangements are also envisaged and in one embodiment and the number of recesses may be as few as three. Each recess 215 has essentially a necked outline with neck portions 220a, b essentially protruding into the void formed by the recess. Neck portions 220a, b allow holding a cable in place once received in the respective recess. The plastic or other material of which base member 205 is formed is thought to have sufficient rigidity that still affords a suitable amount of flexure when the cable is manually pressed into the recesses 215. Upon exertion of force, the two neck portions 220a, b on either side slightly give, that is, flex out of the way of the cable for it to be received at the deeper end of the recess with the neck portions 220a, b then flexing back into their relaxed position when the cable is so received essentially locking the cable into place.

According to one embodiment the recesses 215 are of equal dimension but in other embodiments, for instance the one shown in FIG. 2, the recesses increase in size as one moves along the edge 210. For instance, in the orientation of the spacer 200 as shown in FIG. 2A the recesses increase to either side of 3 and 9 o'clock position and increase in size towards 12 o'clock and 6 o'clock position. At 12 o'clock and 6 o'clock position there is a large recess 280 cutting deeper into the base member 205 than any of the other recesses 215. The large or "double recesses" 280 each have an hour glass shaped appearance with neck portions 285ab. The double recess 280 is essentially a slot capable of receiving in radial direction two or more cables such that a clearance is maintained between the two cables received therein by means of the neck portions 285ab extending or protruding in opposed relationship into the void formed by the double recess 280. Although in FIG. 2A two double recesses 280 are shown, one at 12 o'clock and the other one at 6 o'clock, it will be understood herein that alternative embodiments may include less or more double recesses 280 alongside or instead of the simple recesses 215.

As appreciated from FIG. 2A the arrangement of the plurality of recesses 215 along the spacer's edge gives the spacer a "sprocket" like appearance with the periphery of the recesses meandering about the course defined by the spacer 200's circular edge 210. Looking at the spacer 200 in plan view, the recesses 215, 280 are formed as an alternate sequence of "troughs" and "crests" where the cables are received in their respective troughs and are held therein by two neighboring crests having the necked portions 220ab as explained earlier.

According to one embodiment the spacer 200 also includes openings arranged away from the edge as through holes across the base member 205 for centrally or at least internally receiving cables as opposed to peripherally receiving other cables of the bundle at the recesses 215, 280 formed in the edge.

According to one embodiment the spacer 200 includes two pairs of through holes 250 and 240. The through holes or slots are "internal" in the sense that they are completely surrounded by the material of the base member 205 which is not the case for the "partly open" recesses 215, 280. As shown in FIG. 2 the pairs of slots 240 and 250 can be different in size. Slots 240 and 250 are arranged around a central portion 260.

The slots 240, 250 have, similar to the double recess 280, an hour glass shape with respective neck portions 245a, b and 255a, b respectively. Again, similar to the double recess 280, the slots have a stricture at about the center of its edge defined by the necks 255 and 245ab respectively. Each of the through holes is capable of receiving two cables whilst the neck portions ensure that a clearance is maintained between the cables.

According to one embodiment and as can be seen in FIG. 2A, the spacer is openable so as to allow personnel to conveniently access the inner slots 250 and 240 so as to insert or remove certain of the cables from the cable bundle held or guided by the cable spacer 200. More particularly, the spacer is openable across a split line 230 shown as a dashed line in FIG. 2 that passes through the center portion 260 of the disc 205. There are two inter-lockers 270 shown at either end of the split line. Inter-lockers may be formed as dovetail or snap fit arrangement that allow, without tools, indestructibly opening and closing the spacer 200.

When the spacer 200 is in an open configuration, two wing or jaw portions 200a and 200b are formed which, in the particular embodiment in FIG. 2, are formed by two semi circles. Because of symmetry, the jaws 200a, b are of equally size and shape but again, asymmetric arrangement with different jaw sizes/shapes are also envisaged so long a s commons split can be defined and the two jaws can be safely and securely brought into contact to achieve the closed configuration. However, the large the jaws and the longer the split line, the easier it will be to access the cables. Further, and as can be seen in FIG. 2, the inner through holes or internal slots 240 and 250 essentially extend across the split line and are perpendicular thereto with the split line passing centrally though the internal slots 240,250, in particular pass through the respective neck portions of the through holes 240 and 250. In other words, when the spacer 200 is opened across the split line, the through holes will appear as pairs of matching recesses formed in the edge along the split line in either one of the jaws 200a, 200b. One of the cables can then be inserted or received at those recesses in either jaw portion and after insertion or removal of the cable(s), the jaws 200a, b can be brought in contact to each other and can be closed via the inter-locking members 270. The respective recesses in the split line edge then again unite to form the respective through holes 240, 250. Although in the FIG. 2 embodiment, the through holes 250, 240 are made each up from a pair of two opposed necked recesses formed, one to either side of the split line (that is, they appear to extend thereacross), there are also embodiments where there is only one necked recess formed in one of the jaw portions 200a,b off the slip-line with no recess on the other side of the spit line in the opposing jaw 200a or b. Such a mono-recess is then only able to take up one cable and not two as the slots 250, 240 are configured for. Also, although two pairs are shown any number is envisaged although an even number is preferred for symmetry as the slot can be grouped around the center portion 260. As will be appreciated, the holes and recesses as arranged in the base member 205 preferably in a symmetric manner for a favorable, that is, balanced behavior when taking up torsion. For instance, in FIGS. 2A,B, there are 2 axis of symmetry: one formed by the split line across 3 o'clock and 9 o'clock and one through the 12 o'clock and 6 o'clock orientation.

As can be seen from FIG. 2A and the plan view it affords, the inter-spacings between the various recesses and the necked portions in the respective double recesses and/or through holes 240 and 250 ensure that the cables when received therein are at all times kept at a distance relative to each other to prevent cables from touching each other. Chaffing and other wear and tear on the cables' jackets can thereby be averted as well as undesirable short circuit incidents. It is envisaged herein that the dimensionings of the through holes and recesses, that is their diameters, are such that the cables are slideable through the slots and recesses when received therein so that each cable can slide and bend as the cable bundle is twisted and torsioned to assume configurations at different curvatures as different parts of the cable bundle. The cable spacer serves the function to guide the cables in the cable bundle during their motion.

According to one embodiment the inner periphery of the recesses or slots holes can be lined by a low friction material such as ceramic or aluminum so as to further reduce friction or chaffing as the cables move through the through holes or recesses.

As mentioned earlier the cables in the outer recesses 215 and 280 are held into place by means of the resilient neck portions which are configured to have the required stiffness to maintain their position to securely hold the cables in place. However, in one embodiment there is a retainer ring 290 that is received in the edge of 210 of the cable spacer 200 to further help securing the cables when received in the recesses. According to one embodiment the ring is formed from one piece but in an alternative embodiment there are two semi-rings that each attaches to the respective edge of the wing or jaw portions 200a or b.

As shown in plan view of FIG. 2A, the recess and/or the slots are arranged to circumscribe or enclose the central "hub" portion 260. In other words, the cable bundle when received in the recesses and/or slots, define a volume around the center 260. This allows advantageously absorbing torsion and twist motions when the cable bundle is run between two machine parts that are subjected to relative rotation.

Figure 2B:
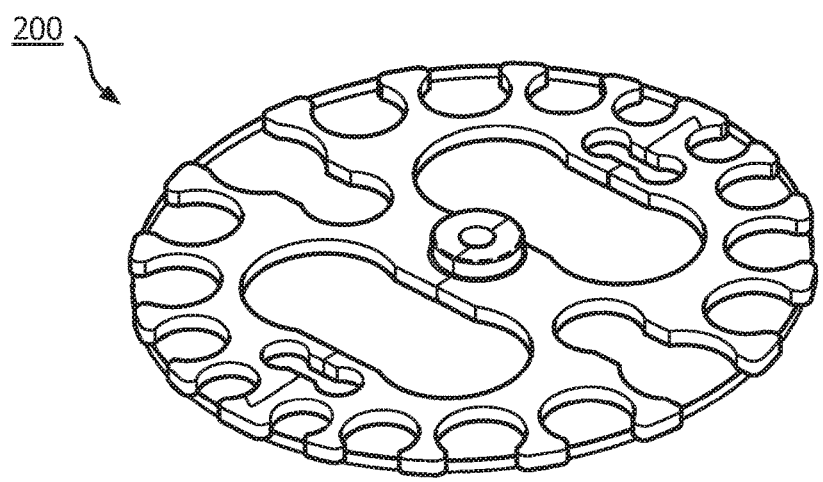

FIG. 2B affords a perspective view on spacer 200 of FIG. 2A.

Figure 3A:
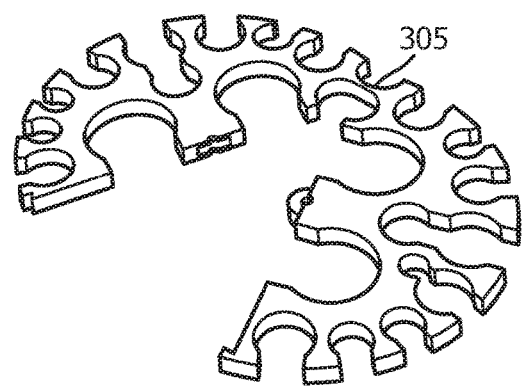
FIG. 3 shows the cables spacer of FIG. 2 in an open or disassembled configuration along with a retainer component.

FIG. 3A shows an alternative embodiment of cable spacer 200. In the embodiment according to FIG. 3A there are no two inter-locking members 270 but only a single one arranged at one end of the split line. At the other end of the split line there is a pivot point 305. In other words the spacer 200 is openable and closeable around the pivot point formed in the edge of spacer 200. In one embodiment the pivot point is articulated. In an alternative embodiment, the pivot point is not articulated by a joint element or similar but pivoting is by means of the material flexibility of which the base member 205 is formed. Yet more particularly, in the not-articulated embodiment, the pivot point is formed in a trough of recess between two neighboring crests or the two jaws 200a,b transition into each other via bridge portion having the required flexibility to take up the pivoting motion when the two jaws are moved into the closed configuration to engage each other. As with the FIG. 3A embodiment, there are other embodiments envisaged herein where the split line does not go from end to end across the base member 205 but may go half way across so that the pivot point may be located not in the edge but away from the base member 205's edge, for instance close to the center portion 260 or (e.g., halfway) between edge 210 and center hub 260. The space may then need to be pried open to achieve the open configuration.

As can be seen in FIG. 3A, in order to ensure a secure fit when the spacer is in a closed position they are arranged along the split line in either edge of the two wing portions 200a,b one or more fiducials for instance in the form of male/female counterparts (such as pin-into-hole) that mate when the spacer is in a closed configuration. In one embodiment the fiducials may also include snap fit arrangements to further increase the fit quality.

Figure 3B:
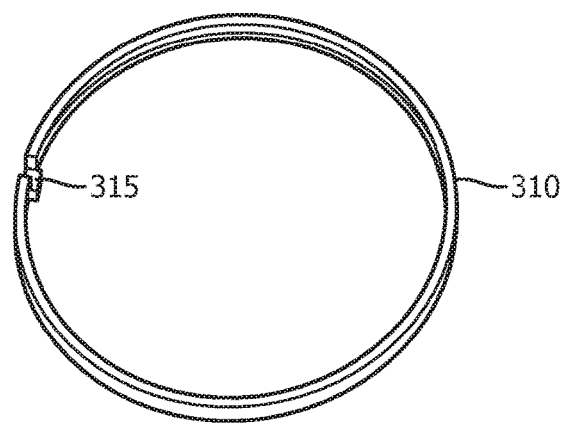

FIG. 3B shows a one piece retainer ring 310 with a snap fit or other interlocker 315. Retainer ring 310 can be used with either FIG. 2 or FIG. 3A embodiment.

Figure 3C:
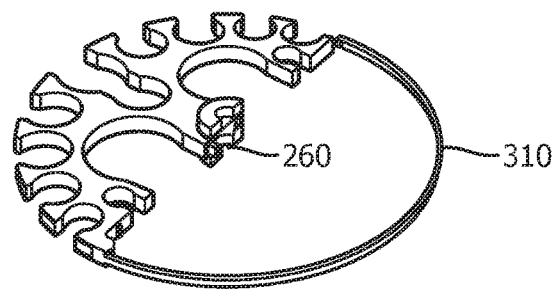
Figure 3D:
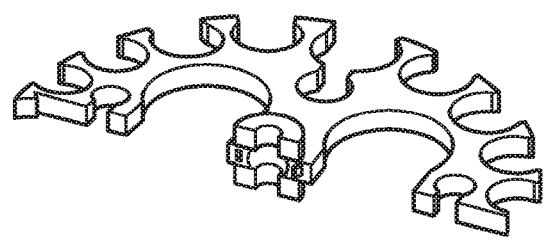

FIG. 3C shows an arrangements where retainer ring is not in one piece as in FIG. 3B but is formed from two semi rings of which one 290 is shown in FIG. 3C opposite one of the wing or jaw portion 200a or b. The semi ring carries in either end a suitable interlocking mechanism with which the ring can interlock the respective wing portion at the respective end of the wing or jaw along the split line 230. The interlocker can be either snap fit dovetail or other suitable inter-locking arrangements that are integral with the spacer structure so in particular do not require tools for its opening or closing.

Figure 4:
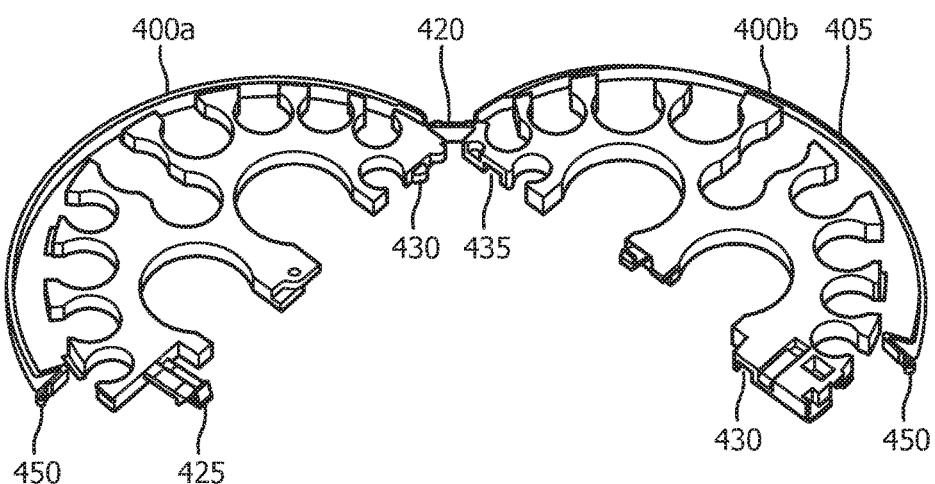
FIG. 4 shows a cable spacer according to yet another embodiment.

With reference to FIG. 4 there is shown an embodiment of the cable spacer where the retainer ring 205 is integrally formed with the cable spacer as a monolithic structure. The general design is very similar to the FIG. 2 embodiment. Also, similar to the FIG. 3a arrangement in FIG. 4, the wing portions include one interlocking mechanism 430, 425 at one end of the split line whereas at the other end there is formed the pivot point 420. A pivot point may be an articulated joint or may be un-articulated similar to FIG. 3A embodiment. The pivot point may again be formed in the trough portion of a respective recess. In yet another embodiment the pivot point is formed by a transition or bridge portion between adjacent crests of two recesses without there being an intermediate recess between the two. In other words, in one embodiment the pivot point 420 is formed in the edge of the base member so is not arranged in the trough of a recess. As can be seen, the structure in FIG. 4 can be understood as the two wing portions 400a, b and the terminal portions of the two retainer semi rings being fused together at the common pivot point 420. Instead of two semi rings, a single ring can be used instead that is cut open carrying at both ends a respective interlocker. Indeed in one embodiment the FIG. 4 spacer is formed by a fusion of those four (or three if the single, cut open ring is used) components but in yet another more preferable embodiment it is envisaged that the spacer in FIG. 4 is formed in one piece as a monolithic structure by cutting or injection molded or is otherwise formed from a single plastic piece. Again, similar to the FIG. 3A embodiment, there may be one or more fiducials points such pin and hole or other male/female counterparts that are arranged in opposed relationship to either side of the split line in the respective edges of the jaw portions 400a, 400b, the male/female counterparts engaging when the jaw portions 400a,b are forced into the closed configuration. There is an interlocking mechanism at one end of the split line in the form of interlocking male/female and/or snap fit dovetail arrangement 425, 430. Also as can be seen in FIG. 4, the loose end of the retainer ring 405 includes a snap fit 430, 450 or similar interlocker that engage the respective end of the respective wing or jaw portion 400a,b. According to one embodiment, the retainer ring can stay engaged when the cable spacer is opened. However, in an alternative embodiment at least one end of the retainer ring 405 will need to be undone before the spacer can be opened by pivoting around the pivot point 420.

Figure 5:
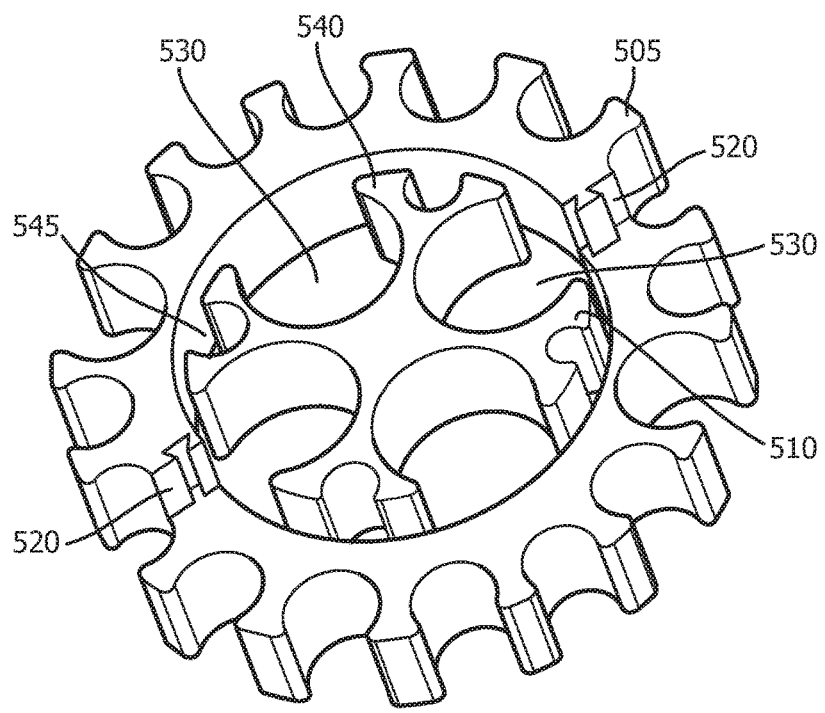
FIG. 5 shows a cable spacer according to yet another embodiment.

With reference to FIG. 5, there is shown a modular or nested design for the cable spacer. The cable spacer includes an inner portion 510 and an outer portion 505. Each of the inner and outer portions 505 and 510 may be designed according to any of the previous embodiments. However, in contrast to the previous designs, the outer part 505 is in the form of an annulus and it is the void so defined where the inner part 510 of the modular cable spacer is received. Put differently, according to one embodiment, the outer part 505 is formed as an annulus having a plurality of at least three recesses arranged at its edge. Again, as in previous embodiments, the recesses have a necked outline to retain the cable when it is in place. The inner portion 510 is essentially a disc as previously described with recesses cut into its edge. In one embodiment the size of the recesses in the inner portion alternate although this may not be so necessarily. In one embodiment, the inner part 510 is formed from a disk with four large recesses 530, forming two opposing pairs or, said differently, the recesses 530 at arranged at 90° relative to each other around the edge. The four recesses 530 are cut into the inner disk as far as they can go without interfering with each so that the remainder of the inner disk has a cross like appearance with mushroom shaped arms 540 into each of which there is cut a smaller slit or recess 545. The terminal portions of those cross arms (with the respective slits therein) about the annulus 505's inner edge when the inner part 510 is inserted into the annulus 505. However this is merely an exemplary design and various modifications are envisaged herein, with or without slits are also with more or less that than the 4 recesses shown. In one embodiment, the inner part's outer edge is recessed as in the FIG. 2 embodiments, or has 2 or more recesses or same size around equidistantly or non-equidistantly round the edge of the inner part 510. The annulus 505 is openable whereupon the annulus disintegrates into two semi-circular parts by sliding the two parts away from each other at a dovetail or other interlocker arrangement520 formed in the edge of the annulus part 505. The inner part 510 is retained in the annular outer part 505 by friction or by having some of the recesses in inner part 510 being slideably receivable in respective ones of a plurality of counterpart ridges formed in the inner edge of annulus' outer part 505.

Figure 6A:
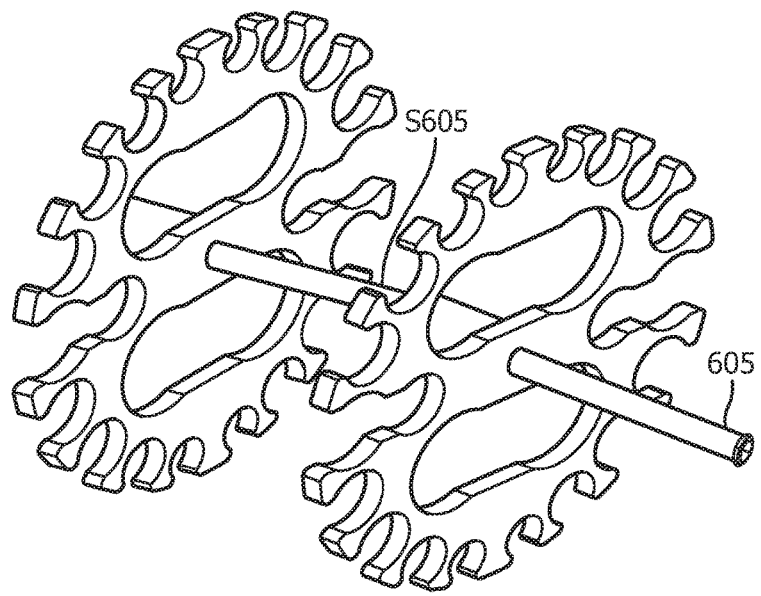
FIG. 6 shows a cable spacer according to a further embodiment.
Figure 6B:
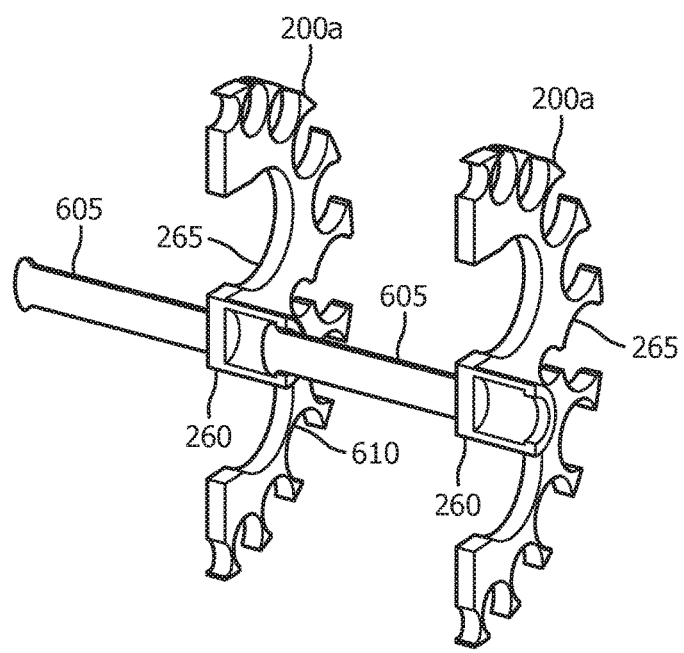

With reference to FIGS. 6A,B there is now shown arrangements where a plurality of the previously described cable spacers can be interlocked to essentially form an at least partly endo-skeletal structure which then at least partly carries or at least guides the free length of the bundle of cables between the bundle's two attachment points. According to one embodiment, there is a plurality of pegs or distance elements 605 arranged between neighboring cable spacers. Although FIG. 6 shows essentially the embodiment of FIG. 2, the interconnecting of a plurality of spacers 200 as shown in FIG. 6 is of equal application to any of the embodiments described herein. Each peg 605 has at least one of its ends a mushrooming head 610 which is receivable in a respective one of the cable spacer's center portion 260. The center portion essentially forms a cavity (which in one, but not necessarily all embodiments, forms a blind hole, that is, it is not a through-hole) where the peg's head 605 is moveable received so that the sequence of pegs so formed can follow a curved outline. Essentially, a ball-and-socket joint connection is thereby afforded. According to one embodiment the pegs 605 are separate from the cable spacers and are on either side clicked into place between two neighboring spacers. However there is also an alternative embodiment as per FIG. 6B where the pegs are integrally formed in one side of the center portion 260. The other side of the center portion 260 is then formed by cavity 265 where then the respective free end of the peg integrally formed with the neighboring spacer is received. In this embodiment, and as shown in FIG. 6A, the split line 270 will run through the respective pegs 605 and cavity hub 206 so that the peg 605 and cavity 206 are each split up in two parts (such as corresponding halves) when the spacer is opened/folded up by moving the two jaws 200a,b away from each other. The spilt line along the peg 605 can be seen as a black line on the rightmost peg 605 in the perspective view of FIG. 6A.

Figure 7:
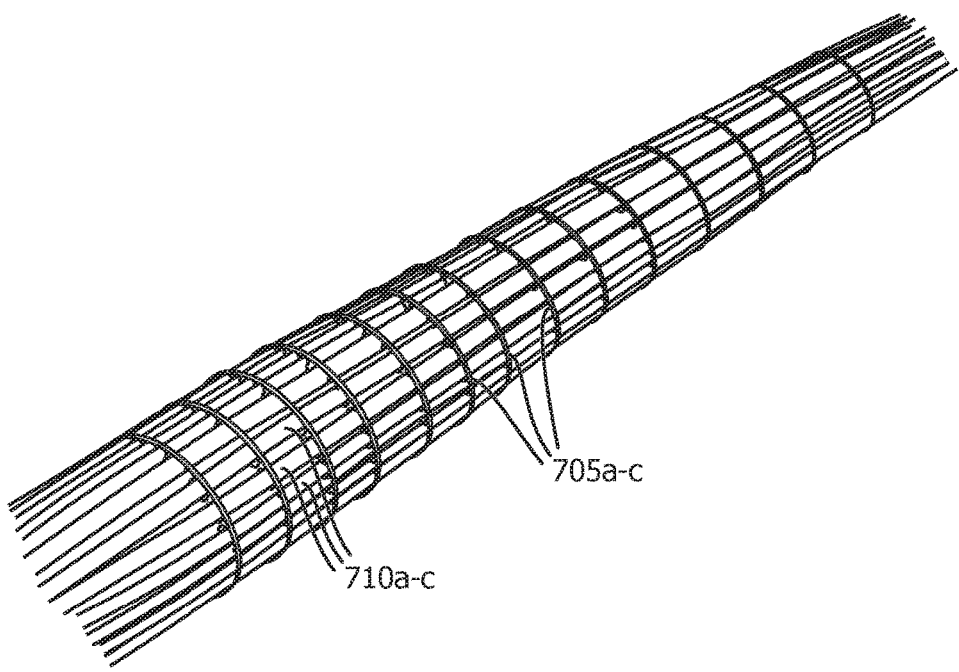
FIG. 7 shows a plurality of cables spacers in the bundle of cables received therein.

FIG. 7 forms a perspective view on the skeletal structure formed by a plurality of cable spacers 705a-c that are arranged along the length of the cable bundle formed by cables 710a-c. As can be seen, the required clearance is maintained between each of the cables, in other words, no two cables are touching at any time even when the cable bundle is made to move in particular when it subjected to torsion, twisting or bending.

Figure 8A:
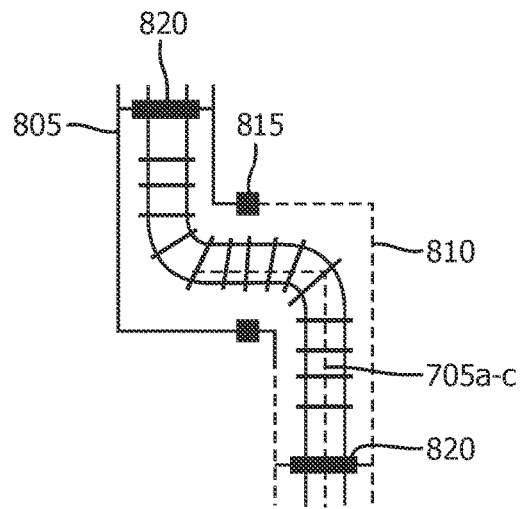
FIG. 8 shows various motions of a bundle of cables held in a cable spacer.
Figure 8B:
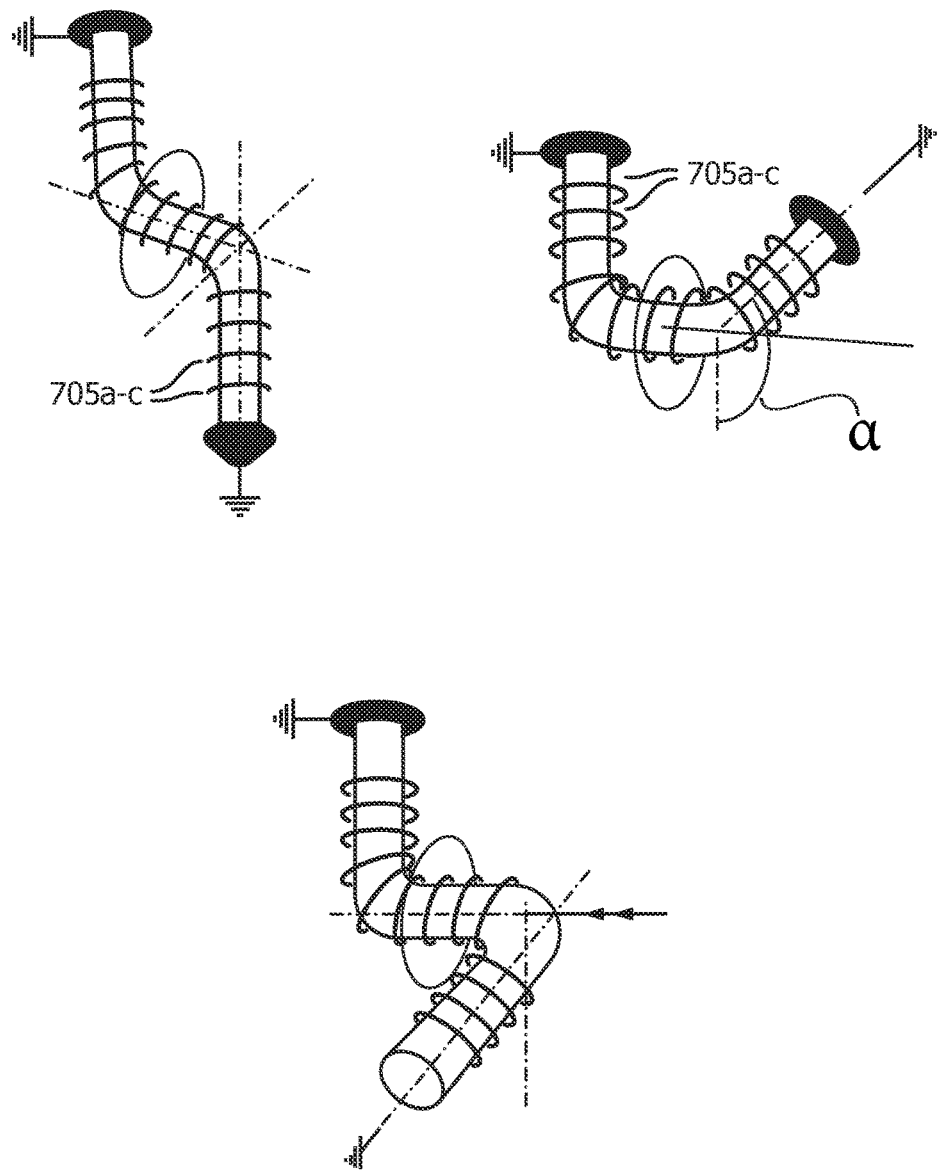

The dynamics of which the spacer skeleton as proposed herein is capable of performing is shown in FIG. 8. According to one embodiment the cable bundle 710a-c forms part of the cable work in a piece of equipment such as medical imager for instance an interventional C- or U-arm imager or any other suitable imager such as CT or other where there is relative rotation between parts connected via the cable bundle 710a-c. For instance, the cables may run between a static part 805 and a moving part 810. The two parts are connected by a suitable bearing 815. However, it is understood that the following is not only applicable for static and moving part but what matters herein is a relative motion between two parts that are connected by cable work. Each end of the cable bundle is assumed to be connected to the respective machine part by suitable strain relief arrangements 820 at the respective end. During operation of the machinery while the parts are moving relative to each other or whilst moving part 810 is moving relative to the static part 805, the cable bundle is subjected to a twisting or torsion around pivot points on the free length of the cable bundle as shown by the angular displacements $-\alpha$, $+\alpha$ in different orientations as per FIG. 8B. The respective pivot points around which the whole cable bundle pivots is shown in FIG. 8b by means of a circle. It is precisely the strain on the cable bundle at the pivot points which is favorably absorbed and in fact made possible by the cable spacer arrangement as proposed herein. As can be seen, the cables never touch at no point along their length within the spacers during the motion because the required mutual security clearance is always maintained by way of the mutual distances between the recesses and/or through holes formed in the respective cable spacers. The cables are allowed to slide through the cable holes as the cable twisted by the rotational motion of the moving part relative to the static part. This dynamic arrangement afford by the interconnected system of the sequence of cable spacers allows accommodating the various curvatures at different parts of the bundle that are assumed during the motion of the cable bundle. Note that more complicated motions are also possible and the inter-cable clearances are still maintained. For instance, the two machine parts between which the cable bundle runs may not only rotate relative to each other but may move to and fro towards and/or away from each other.

Figure 9:
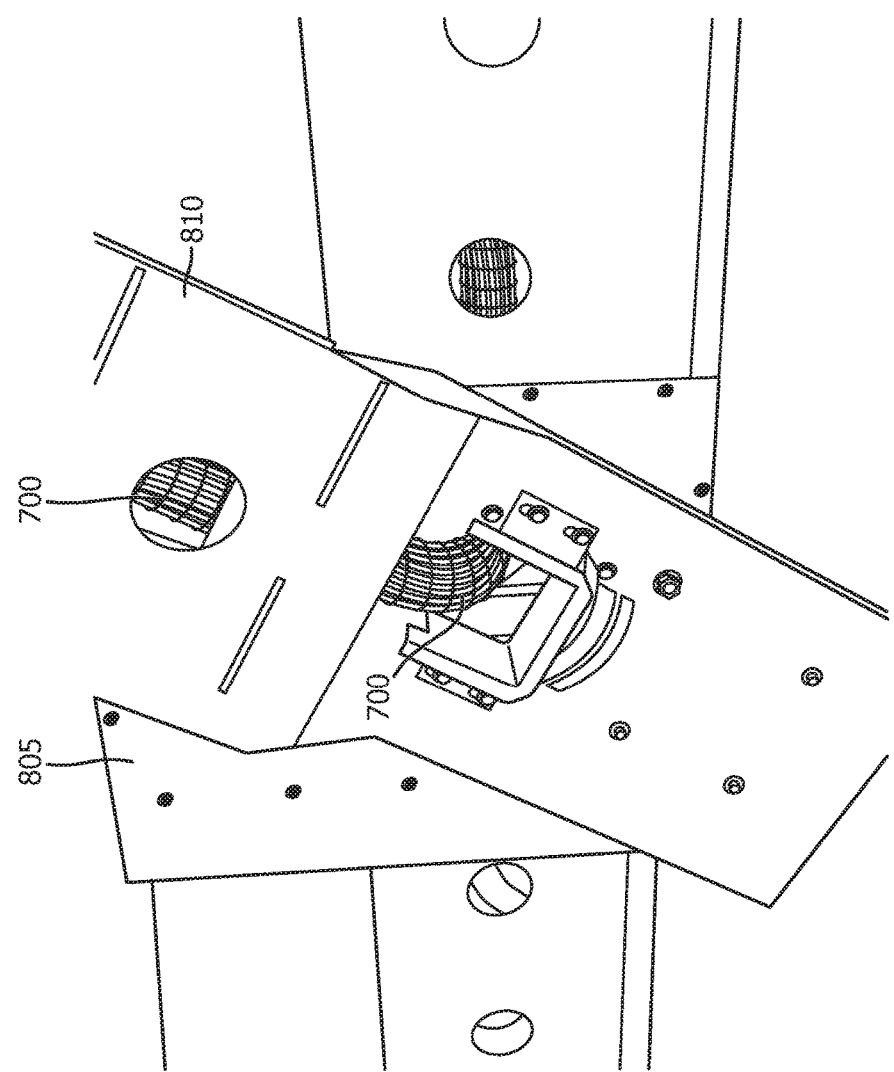
FIG. 9 shows the cable spacer arrangement of FIG. 8 run insides the rotating system.

With reference to FIGS. 9,10 there is shown a test arrangement with a cable bundle 700 where the cable spacer skeletal arrangement of FIGS. 7,8 is run internal of a piece of equipment. The cable bundle with its cable spacer's skeletal is run in channels, chutes or frames internal to the machinery equipment. The actual housing or covering has been removed in FIG. 9 to better show how the cable bundle snakes its way inside the machinery. Note the rotation taken up by the cable bundle inside spacer system arrangement as shown in FIG. 10 where the moving part 810 is a square shaped frame piece to which one end of the bundle is connected via a strain relief connector (not shown). In the lower image of FIG. 10, the square frame (and hence the bundle in the spacer arrangement) is rotated by 45° (that is, has its corner pointing downwards) relative to the configuration in the upper image of FIG. 10.

As an alternative embodiment to FIG. 8 where the distances between neighboring spacers are maintained by way of the pegs there is an alternative embodiment where the center portions 260 of each cable spacer is formed by a through hole through which a central cable (of the bundle) is run. The individual cable spacers are then fixed onto that central cable by a suitable fixing mechanism. It is by fixing immovably the respective cable spacers along said central cable that the distance between neighboring cable spacers is maintained. In the embodiment with pegs 605, the cable spacer disks 200 are not fixed onto any of the cable but the inter spacer distances through the spacer arrangement (see FIGS. 6 and 7) are maintained due to the pegs' 605 rigidity. The pegs 605 prevent the shifting of the spacers along the cable length. In one embodiment, the pegs have a length of 2-5 cm or even larger although these numbers or purely for illustration and not limiting. In a typical application the skeletal spacer system may be formed from 20-50 different spacers. Having the spacers arranged at distances between each other allows forming or defining section of free cable lengths between the spacers. The free length define sections of volumes (for instance cylindrical as FIG. 7 shows) and it is those volumes or free length cable section that allows absorbing the torsions. For instance cables away from the center of the bundle can assume a smaller curvature than those cables situated more towards the center because the individual cables in the bundle are allowed to independently slide within or through the recesses/holes/slots in which they are retained.

In one medical embodiment, the cable bundle in the spacer arrangement is run internal to an interventional C-arm imager of the type shown in FIG. 1. In one embodiment, the bundle is run between arm and cradle/sleeve of the interventional imager. The cable bundle runs internally for instance on the hollow C-am whilst the cables in the bundle are spaced apart from each other by the sequence of cable spacers as described herein. Use in a CT gantry is also envisaged.

In short, the embodiments described above form a cable guiding solution for situations where free lengths of cables are required to pass through one or more pivot point between a moving part and a static part or between parts where there is relative motion. On both parts, the cables are fixated by means of a strain relief. In the moving free lengths, the cables are separated by spacers as described herein to achieve minimal friction/chaffing between cables. The free cable lengths between the spacers can absorb the torsion and bending displacement due to the movement.

Other applications outside medical context are also envisaged for instance in construction equipment or robotics in particular animal or humanoid robots or industrial robots used in manufacturing facilities. For instance, electrical or hydraulic cable work may now safely run inside (articulated) robot arms/limbs, gripper or frame, etc.

It has to be noted that embodiments of the invention are described with reference to different subject matters. In particular, some embodiments may be described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A cable spacer for receiving at least partly a plurality of cables, configured to maintain a clearance among the cables during motion of at least one of said cables or during motion of the cable spacer, the cable spacer comprising:
   at least three recesses formed in an edge of said cable spacer for receiving at least three cables, said at least three recesses being arranged so as to enclose a central area of the cable spacer;
   a peripheral retainer ring member at least in a part removably receivable around the edge to hold in place at least one cable when received in one of the recesses, wherein the peripheral retainer ring member and the cable spacer are a monolithic structure; and
   a slot, which is surrounded by a material of the cable spacer, the slot having an hour glass shape compromising neck portions.

2. The cable spacer of claim 1, the cable spacer being openable and closable, the cable spacer forming two jaw portions when open so as to receive a cable or to allow removal of a cable, with mating closure elements formed in the jaw portions that are configured to engage when the jaw portions are moved into contact to close the cable spacer.

3. The cable spacer of claim 2, wherein the jaw portions are wing portions, the wing portions being fused together at a common pivot point, the cable spacer being openable and closable around said common pivot, point.

4. The cable spacer of a 3, wherein the common pivot point is formed in said edge or away from said edge.

5. The cable spacer of claim 1, wherein the edge is curved or wherein the cable spacer is formed from an oval or spherical disk when closed.

6. The cable spacer of claim 1, further comprising a plurality of through-holes arranged so as to enclose the central area.

7. The cable spacer of claim 2, each jaw portion having a necked recess, the necked recesses providing a necked through-hole through the cable spacer when the cable spacer is closed, the necked through-hole for receiving two or more cables prevented from touching each other by at least one neck portion formed in a periphery of at least one the necked recesses.

8. The cable spacer of claim 2, wherein the closure elements are any one of i) a snap fit or ii) a dovetail arrangement.

9. The cable spacer of claim 1, wherein the cable spacer comprises a plastic material.

10. The cable spacer of claim 1, wherein the central area includes a blind hole for receiving an end of an elongate distance element.

11. The cable spacer of claim 1, having an elongate distance element integrally formed therewith at the central area, the elongate distance element extending away from the cable spacer.

12. A spacer arrangement for receiving a plurality of cables, comprising a plurality of spacers according to claim 1 arranged along a length of the cables at a distance to each other when the spacer arrangement is in use.

13. Medical imaging equipment or other machinery, comprising:
   at least one movable component with a plurality of cables connected to said at least one moveable component, the plurality of cables being moved when said at least one moveable component is moving, the plurality of cables received in at least one cable spacer as per claim 1 or received in a spacer arrangement wherein the cables so received are run internally in a housing of the medical imaging equipment or other machinery.

14. The cable spacer of claim 2, wherein an end of the peripheral retainer ring member includes an interlocker configured to engage a respective end of a respective wing portion or jaw portion.

15. The cable spacer of claim 1, wherein at least two of the at least three recesses are not a same size.

16. The cable spacer of claim 1, further comprising a double recess.

17. The cable spacer of claim 16, wherein the double recess has an hourglass shape.

* * * * *